(12) United States Patent
Kinney et al.

(10) Patent No.: US 8,346,362 B2
(45) Date of Patent: Jan. 1, 2013

(54) MOLDED HEADER CONNECTED TO A MEDICAL DEVICE BY LATERAL DEFORMATION OF A SLEEVE/FEEDTHROUGH PIN SUB-ASSEMBLY

(75) Inventors: James Kinney, Clarence, NY (US); James Coffed, Depew, NY (US); Gabriel A. Kustra, Cheektowaga, NY (US)

(73) Assignee: Greatbatch Ltd., Clarence, NY (US)

( * ) Notice: Subject to any disclaimer, the term of this patent is extended or adjusted under 35 U.S.C. 154(b) by 685 days.

(21) Appl. No.: 12/475,643

(22) Filed: Jun. 1, 2009

(65) Prior Publication Data

US 2010/0038132 A1    Feb. 18, 2010

Related U.S. Application Data

(60) Provisional application No. 61/088,465, filed on Aug. 13, 2008.

(51) Int. Cl.
*A61N 1/00* (2006.01)
(52) U.S. Cl. ........................... 607/37; 607/36
(58) Field of Classification Search .............. 607/36–38; 439/289, 669; 174/659
See application file for complete search history.

(56) References Cited

U.S. PATENT DOCUMENTS

| | | | | |
|---|---|---|---|---|
| 4,934,366 A | * | 6/1990 | Truex et al. ..................... | 607/37 |
| 6,157,531 A | * | 12/2000 | Breyen et al. .................. | 361/519 |
| 7,630,768 B1 | * | 12/2009 | Coffed et al. .................. | 607/37 |
| 2008/0009912 A1 | * | 1/2008 | Spadgenske .................... | 607/37 |

FOREIGN PATENT DOCUMENTS

| | | |
|---|---|---|
| EP | 191556 | 3/2002 |
| EP | 1695736 | 8/2006 |

OTHER PUBLICATIONS

European Search Report—Application No. 09167804.5-2305, dated Nov. 2009.

* cited by examiner

*Primary Examiner* — Christopher D Koharski
*Assistant Examiner* — Catherine Voorhees
(74) *Attorney, Agent, or Firm* — Michael F. Scalise (57) ABSTRACT

A header assembly for connecting an implantable medical device to at least one conductor lead terminating within a patient intended to be assisted by the medical device is provided. The implantable medical device is comprised of numerous feedthrough wires in a dense, non-linear, scattered format extending from the control circuitry and through a wall of the housing. The header assembly is comprised of an insulative body that is mountable on the housing of the medical device. The insulative body supports at least one conductor subassembly comprising a terminal that is directly connectable to the conductor lead, an intermediate conductor wire comprising a distal end connected to the terminal and a proximal end connected to a connector sleeve. Methods for making the header assembly and for connecting the header assembly to the implantable medical device are also disclosed.

12 Claims, 9 Drawing Sheets

MOLDED HEADER CONNECTED TO A MEDICAL DEVICE BY LATERAL DEFORMATION OF A SLEEVE/FEEDTHROUGH PIN SUB-ASSEMBLY

CROSS-REFERENCE TO RELATED APPLICATION

The present invention claims priority from U.S. provisional Application Ser. No. 61/088,465, filed Aug. 13, 2008.

BACKGROUND OF THE INVENTION

1. Field of the Invention

The invention relates to a molded polymeric header assembly for connecting an implantable medical device to a body organ assisted by the medical device. More particularly, the present invention relates in one embodiment to a method for making a header assembly in which the embedded electrical connectors are precisely located in a dense arrangement within the molded polymeric header body.

2. Prior Art

Implantable medical devices have feedthrough conductors in the form of pins or wires connected to the internal components of the medical device. The feedthrough wires extend through a wall of the medical device housing and are electrically insulated there from by a ceramic-to-metal seal or a glass-to-metal seal. Electrical continuity to a conductor lead attached to the body being assisted is established by connecting intermediate conductor wires supported by a polymeric header mounted on the medical device to the feedthrough wires of the implantable device and terminal blocks in the molded header body. The terminal blocks then provide for plugging the conductor lead into the molded polymeric header. Examples of this type of header assembly are shown in U.S. Pat. Nos. 4,254,775 to Langer, 4,262,673 to Kinney et al., 4,764,132 to Stutz, Jr., 5,282,841 to Szyszkowski and 5,336,246 to Dantanarayana. The disclosures of these U.S. patents are incorporated herein by reference.

U.S. Pat. No. 7,167,749, issued Jan. 23, 2007 to Biggs et al., which is assigned to the assignee of the present invention and incorporated herein by reference, discloses a header assembly comprising a body of polymeric material supporting at least one unitary conductor wire. The header may have multiple conductor wires. The conductor wires connect between feedthrough wires exiting the medical device and terminal blocks into which conductor leads plug.

Implantable medical devices have become more complex in recent years. In addition to providing a stimulus or other beneficial treatment to a body organ, the devices may include sensors and/or remote imaging devices which are to be connected to the circuitry within the device casing. The devices may also perform more than one medical function. Due to the growing complexity of implantable medical devices, there is a need for a header that provides a greater number of electrical connectors for leads and sensors that are connected to the device. The size of the header must be maintained approximately constant, with the electrical connectors closely spaced therein. There is thus a need for a molded polymeric header in which the electrical wires and terminal blocks are located with a high degree of precision. This is so a reliable electrical connection can be made with all of the associated feedthrough wires exiting the medical device. There is also a need for a method to connect a medical device having a complex array of feedthrough wires to a header with a correspondingly complex array of electrical conductors.

SUMMARY OF THE INVENTION

Accordingly, embodiments of the present invention are provided that meet at least one or more of the following objects.

It is an object of this invention to provide a molded polymeric header assembly for an implantable device wherein the assembly has a high density, and preferably non-linear and scattered, of electrical connectors precisely located and embedded therein.

It is a further object of this invention to provide tools, apparatus, and methods for making a molded polymeric header assembly with a high density of electrical connectors precisely located and embedded therein, and for connecting such a header assembly to an implantable medical device.

According to the present invention, therefore, a header assembly for connecting an implantable medical device to at least one conductor lead terminating within a patient intended to be assisted by the medical device is provided. The implantable medical device is comprised of a housing containing control circuitry, at least one electrical energy storage device, and a plurality of non-linear, scattered feedthrough wires, wherein one of the wires as viewed from the side is at least partially blocked by another wire(s), capable of extending from the control circuitry and through a wall of the housing. The header assembly is comprised of an insulative body that is mountable on the housing of the medical device, and at least one conductor subassembly comprising a terminal supported by the insulative body, wherein the terminal is directly connectable to the at least one conductor lead; an intermediate conductor wire comprising a distal end connected to the terminal, and a proximal end; and a connector sleeve. Each connector sleeve includes an outer surface, a distal end including a distal bore, a central region, and a proximal end including a proximal bore. The distal end of each connector sleeve is supported by the insulative body, the proximal end of the intermediate conductor wire is disposed within the distal bore of the connector sleeve, and the proximal bore of each connector sleeve is connectable to a corresponding feedthrough wire that will be a part of the implantable medical device. In the preferred embodiment, a connection inlet is provided in the bottom surface of the insulative body, and the proximal end of the connector sleeve including its proximal bore and the through hole therein are disposed within the gap formed between the connection inlet of the insulative body and the medical device. In this manner, the proximal end of the connector sleeve is exposed, and may be connected to the at least one feedthrough wire by a joining operation, for example anyone of a number of mechanical force connection techniques such as crimping and/or resistance welding.

The insulative body of the header assembly is preferably of a molded polymeric material. The terminal, the intermediate conductor wire, and the connector sleeve of the at least one conductor subassembly may consist essentially of titanium. The connector receptacle preferably has an original cylindrical shape. The medical devices to which the instant header assembly may be fitted include, but are not limited to, a hearing assist device, a neurostimulator, a cardiac pacemaker, a drug pump, a cardiac defibrillator, and an obesity control device.

Also according to the present invention, there is provided a method for making a header assembly for connecting an implantable medical device to at least one conductor lead terminating within a patient intended to be assisted by the medical device. The method comprises the steps of providing at least one conductive connector receptacle comprising an outer surface, a distal end including a distal bore, a central region, and a proximal end including a proximal bore; providing a feedthrough adapter holder/interconnector comprised of two slidable, plate shaped bodies wherein each body includes an upper surface, a lower surface, a side wall, and at least one through bore extending from the upper surface to the lower surface of the entire feedthrough adapter holder/interconnector. The method includes the steps of providing the through hole having a diameter sized to enable a press fit of the conductive connector sleeve therein; fitting the conductive connector sleeve into the through bore such that the plate shaped bodies of the feedthrough adapter holder are engaged with at least the central section of the conductive connector sleeve; moving the feedthrough adapter holder/interconnector so that it is engaged with the proximal end of the conductive connector; providing at least one conductor wire comprising a distal end and a proximal end, and inserting the proximal end of the conductor wire into the distal bore of the conductive connector sleeve, and joining them together; positioning the conductor wire in a fixture so that its distal end is joinable to a terminal; providing at least one terminal, and joining the terminal to the distal end of the conductor wire to form at least one conductor subassembly comprising the conductive connector sleeve, the conductor wire, and the terminal; placing the at least one conductor subassembly in a mold cavity; molding a monolithic polymeric header body around the at least one conductor subassembly to form the header assembly; and removing the header assembly from the mold.

The step of placing the at least one conductor subassembly in a mold cavity may include engaging the terminal with a mold insert provided in the shape of a conductor lead connector, so as to form an opening in the polymeric header body for connecting a conductor lead to the terminal. This step may alternatively or additionally include placing a mold insert within the mold cavity, wherein the mold insert comprises a recessed cavity comprising a bottom surface and a side surface terminating at an upper surface. The feedthrough adapter holder/interconnector is disposed in the recessed cavity such that the bottom surface of the recessed cavity is contiguous with the lower surface of the feedthrough adapter holder/interconnector, and the side surface of the recessed cavity is continuous with the side wall of the feedthrough adapter holder/interconnector. The upper surface of the feedthrough adapter holder/interconnector may be located below the upper surface of the mold insert and within the recessed cavity, thereby forming a boss cavity. The resulting molded header body comprises an extended boss formed within the boss cavity. Additionally, the through hole in the feedthrough adapter holder/interconnector may have a counter bore, and the bottom surface of the recessed cavity in the mold insert may have at least one pedestal disposed in the counter bore of the through hole in the feedthrough adapter holder/interconnector.

The header made according to the instant method may be comprised of a plurality of subassemblies similar to the one described above. The feedthrough adapter holder/interconnector may comprise, or consist essentially of, polysulfone polymeric material, or polyetheretherketone polymeric material. The terminals, the intermediate conductor wire, and the connector sleeve of the conductor subassemblies may comprise, or consist essentially of, titanium or other suitable conductive materials.

The conductor wires of the conductor subassemblies may be pre-formed into the desired shapes to be supported within the polymeric header body prior to the step of positioning the conductor wires in the fixture. The step of joining a conductor wire to a conductive connector sleeve may be performed by laser welding, press fitting and/or resistance welding the proximal end of the conductor wire into the distal bore of the connector sleeve.

Also according to the present invention, there is provided a method for connecting a header assembly to an implantable medical device, comprising the steps of providing the implantable medical device having a housing containing control circuitry, at least one electrical energy storage device, and at least one feedthrough wire extending from the control circuitry and through a wall of the housing after the feedthrough wire is interconnected to the connector sleeve, and providing the header assembly comprised of an insulative body that is mountable to the housing of the medical device, and at least one conductor subassembly. The conductor subassembly is comprised of a terminal supported by the insulative body, an intermediate conductor wire comprising a distal end connected to the terminal, and a proximal end, and a connector sleeve. The connector sleeve includes an outer surface, a distal end including a distal bore, a central region, and a proximal end including a proximal bore, wherein the distal end of the connector is supported by the insulative body, the proximal end of the intermediate conductor wire is disposed within the distal bore of the connector sleeve, and the proximal end of the connector is exposed in a recess in the bottom surface of the insulative body.

The method further includes the steps of positioning the header assembly proximate to the implantable device wherein the distal end of at least one feedthrough wire, not interconnected to the implantable device at this time, is disposed in the proximal bore of the connector sleeve of the at least one conductor subassembly, and the bottom surface of the insulative body is proximate to the wall of the housing of the implantable medical device after the feedthrough wire is interconnected to the connector sleeve; and at least one crimping device applying sufficient pressure through the feedthrough adaptor holder/interconnector to the distal end of the at least one feedthrough wire received in the proximal bore of the connector sleeve, and thereby crimping the connector sleeve to the feedthrough wire.

In one embodiment, the implantable device and the header assembly may be configured such that after performing the step of positioning the header assembly proximate to the implantable device, an interstice is present between at least a portion of the bottom surface of the insulative body proximate the wall of the housing of the implantable medical device. In this embodiment, the step of sealing the bottom surface of the insulative body to the wall of the housing of the implantable medical device may be performed by filling the interstice with a curable liquid sealant. The resulting cured liquid sealant may consist essentially of an organopolysiloxane.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which:

FIGS. 6A and 6B are cross-sectional views of a header assembly including the conductor subassemblies and the molded header body that show the feedthrough adapter holder/interconnector remaining attached to the conductive connector sleeves of the header assembly after the mold is removed; FIG. 6A also illustrates the medical device's feedthrough wires positioned in the connector and FIG. 6B illustrates the medical device's feedthrough wires crimped with the connector sleeves.

FIG. 8 is a cross-sectional view of the header assembly connected to an implantable device, including a seal provided there between;

The present invention will be described in connection with preferred embodiments, however, it should be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION OF THE PREFERRED EMBODIMENTS

For a general understanding of the present invention, reference is made to the drawings. In the drawings, like reference numerals have been used throughout to designate identical elements.

Figure 1:
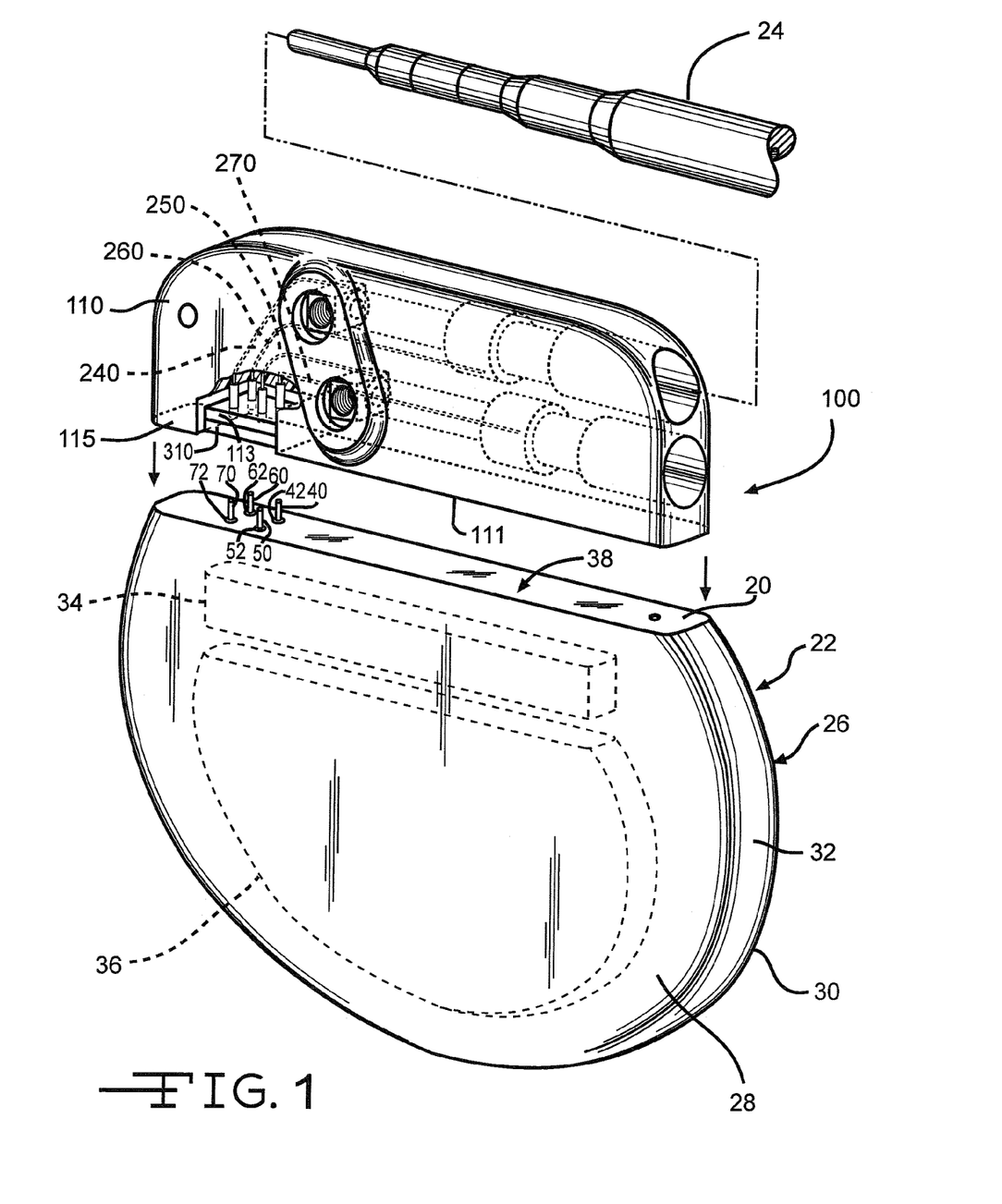
FIG. 1 is an exploded view of a header assembly mounted on an implantable medical device according to the present invention.

FIG. 1 is an exploded view of a header assembly mounted on an implantable medical device according to the present invention. Implantable medical device 22 comprises a housing 26 of a conductive material, such as of titanium or stainless steel. Preferably, the medical device housing 26 is comprised of mating clam shells in an overlapping or butt welded construction, as shown in U.S. Pat. No. 6,613,474 to Frustaci et al. This patent is assigned to the assignee of the present invention and incorporated herein by reference. The housing 26 can also be of a deep drawn, prismatic and cylindrical design, as is well known to those skilled in the art.

The housing 26 is shown in an exemplary form comprising first and second planar major face walls 28 and 30 joined together by a sidewall 32 and the header wall 20. The sidewall 32 curves from one end of the header wall 20 to the other end and is generally arcuate from face wall 28 to face wall 30. The preferred mating clam shells of housing 26 are hermetically sealed together, such as by laser or resistance welding, to provide an enclosure for the medical device including its control circuitry 34 and a power supply 36, such as a battery (the control circuitry and power supply are shown in dashed lines in FIG. 1). The power supply 36 is connected to the control circuitry 34 by electrical leads (not shown). There may also be a capacitor for a medical device such as a defibrillator. The implantable medical device 22 is exemplary of any one of a number of known assist devices such as cardiac defibrillators, cardiac pacemakers, drug pumps, neurostimulators, hearing assist devices, and the like.

Header wall 20 of housing 26 has a planar upper surface 38 providing at least one opening through which a feedthrough wire passes. In the embodiment depicted in FIG. 1, the upper surface 38 of housing 26 includes four openings through which respective feedthrough wires 40, 50, 60, and 70 pass. Four feedthrough wires are illustrated for ease of illustration, however, it is understood that more or less feedthrough wires can be used in the present invention.

The feedthrough wires extend from a proximal end positioned inside the housing 26 connected to the control circuitry 34 to respective distal ends spaced above, as illustrated, the housing upper surface 38. The feedthrough wires 40, 50, 60, and 70 are electrically insulated from the housing 26 by respective ceramic-to-metal seals or glass-to-metal seals 42, 52, 62, 72, as are well known by those skilled in the art.

Header assembly 100 is comprised of an insulative body 110 that is mountable along bottom surface 111 on the housing 26 of the medical device 22, and at least one conductor subassembly comprising a terminal supported by the insulative body 110. The terminal is directly connectable to at least one conductor lead 24. The conductor subassembly further comprises a plurality of intermediate conductor wires 240, 250, 260, 270. Each intermediate conductor wire has a distal end connected to a terminal and a proximal end connected to a respective connector sleeve 140, 150, 160, 170, as shown in FIGS. 4, 5, 6A and 6B. A gap 113 (see FIGS. 1 and 5) is provided at the bottom surface 111 of the insulative body 110, and the proximal ends of the connector sleeves 140, 150, 160, 170 are disposed within the gap 113, as will be described subsequently herein.

Much of the structure of header assembly 100 is similar to the header assembly 10 of the aforementioned U.S. Pat. No. 7,167,749 of Biggs et al. and will not be recited again in this disclosure. However, a major difference between the competing header assemblies is the manner in which the conductor wires 140, 150, 160, 170 are connected to the feedthrough wires of the implantable device using the respective intermediate connector sleeves 140, 150, 160, 170, as will be explained presently. In the following disclosure, methods for making the header assemblies of the present invention and connecting them to implantable devices will be described. In providing the description of these methods, the structure of the header assemblies will also be described.

Figure 2:
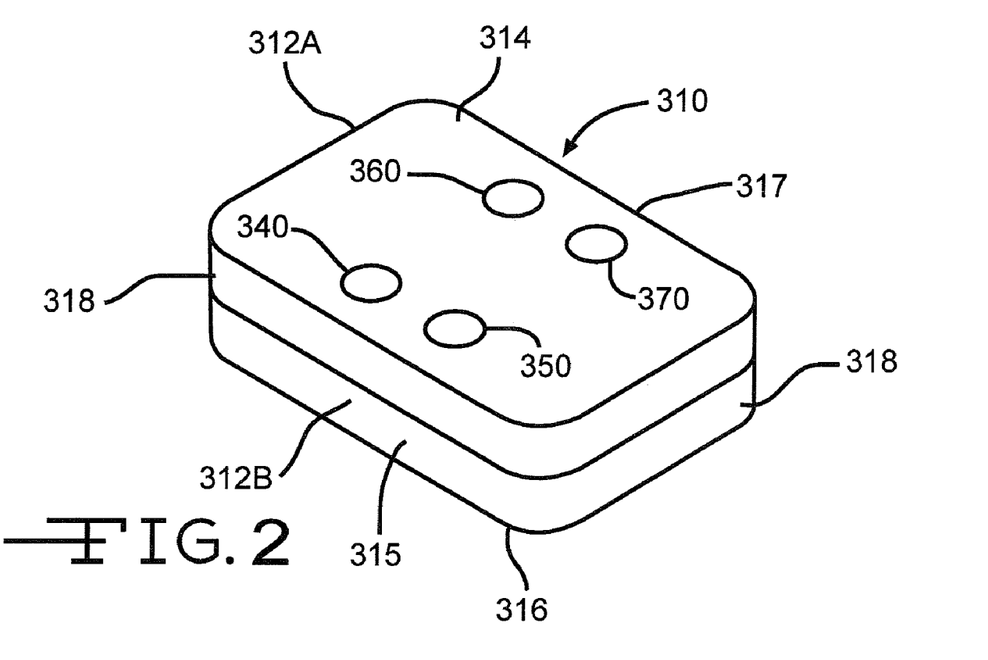
FIG. 2 is a perspective view of a feedthrough adapter holder/interconnector used in making the header assembly of the present invention and interconnecting the implantable medical device's feedthrough wires to the header assembly's conductive connector sleeves.
Figure 3:
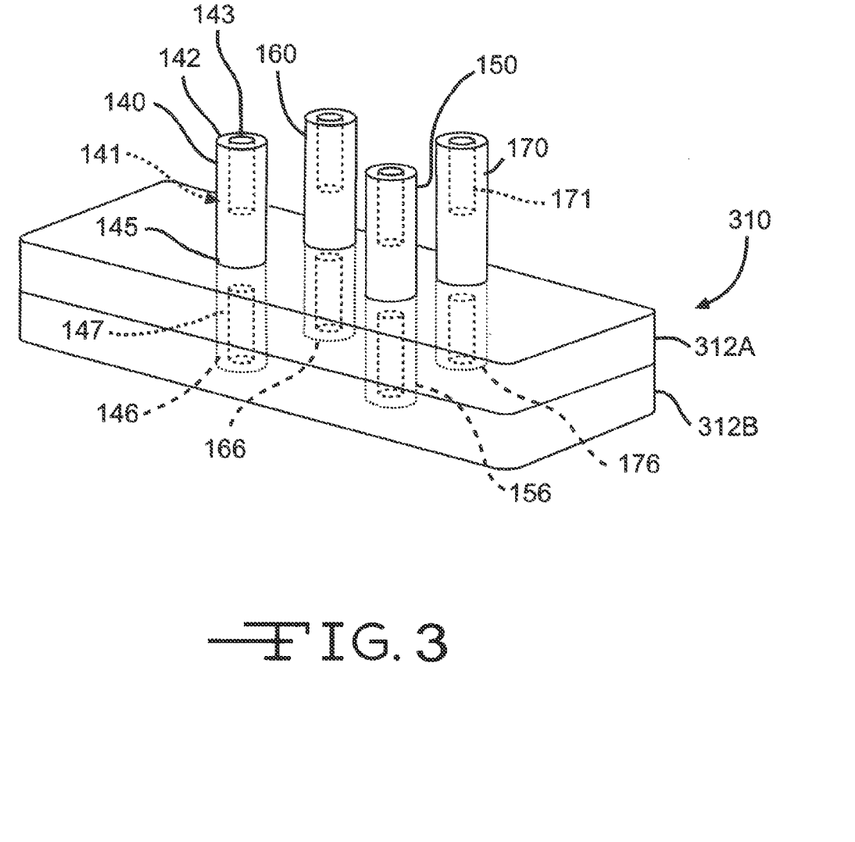
FIG. 3 is a view of the feedthrough adapter holder/interconnector of FIG. 2, with conductive connector sleeves of the header assembly press fitted within through holes therein.
Figure 4:
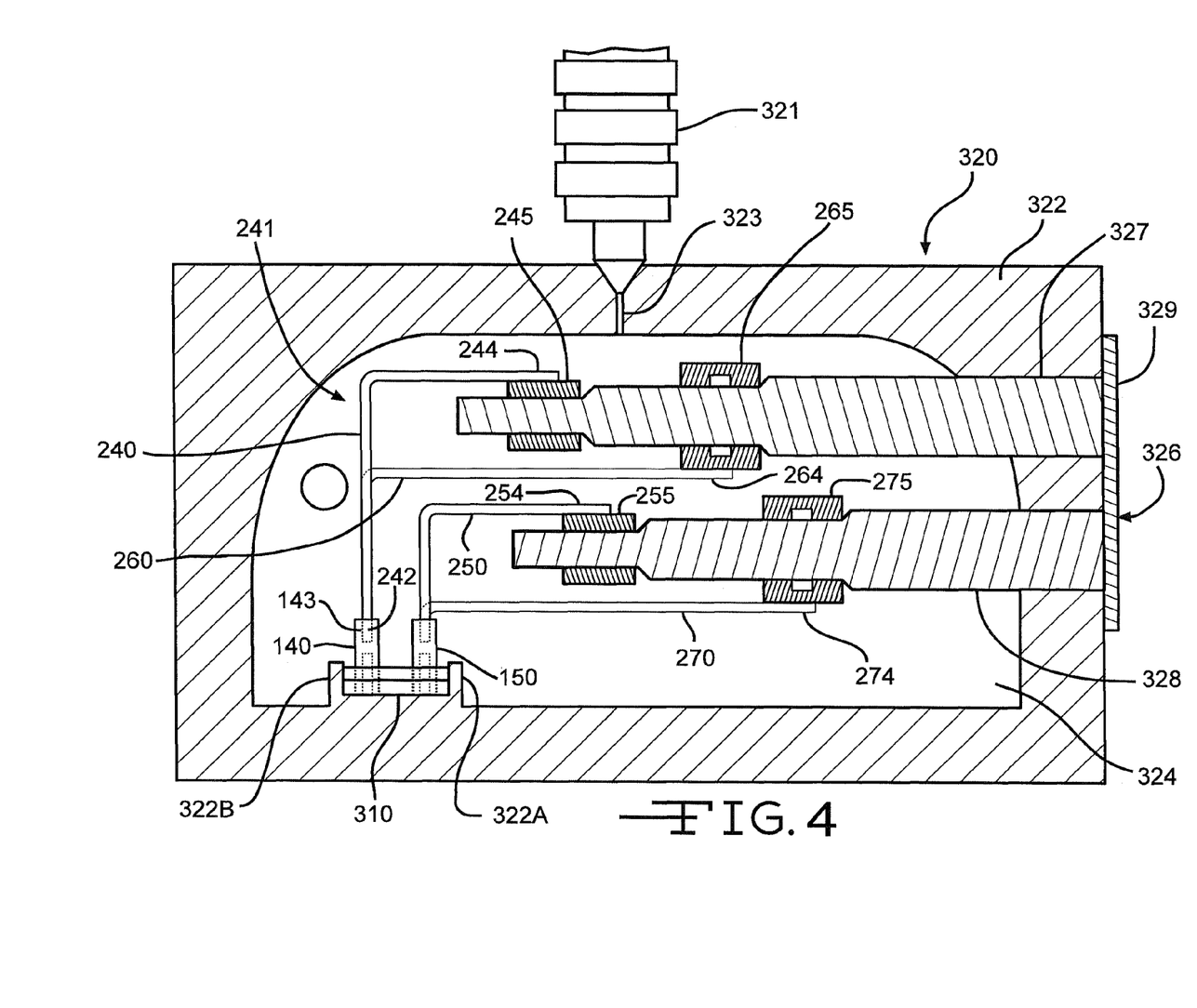
FIG. 4 is a perspective view of the feedthrough adapter holder/interconnector and conductive connector sleeves of FIG. 3.

FIG. 2 is a perspective view of a feedthrough adapter holder/interconnector 310 used in making the header assembly and connecting the header assembly 100 to the implantable medical device 22; FIG. 3 is a view of the feedthrough adapter holder/interconnector 310 of FIG. 2, with conductive connector sleeves 140, 150 of the header assembly 100 fitted within through holes therein; and FIG. 4 is a perspective view of the feedthrough adapter holder/interconnector 310 and connector sleeves of FIG. 3 in the housing mold 320. A feedthrough adapter holder/interconnector 310 is provided comprising an upper slidable plate shaped body 312A, and a lower slidable plate shaped body 312B. Each slidable plate shape body has an upper surface 314, a lower surface 316, a front wall 315, a back wall 317, opposing side walls 318, and through holes 340, 350, 360, and 370 extending from the upper surface 314 to the lower surface 316. Moreover, each through hole in one plate shaped body aligns with a corresponding through hole in the other slidable plate shape body.

Feedthrough adapter holder/interconnector 310 is made of an insulative material that can crimp, with the assistance of a crimping tool to be described later, the connector sleeves to the feedthrough wires. The holder/interconnector 310 is an insulator and may consist essentially of polysulfone polymeric material, or polyetheretherketone polymeric material.

In the exemplary embodiment shown in the figures, four conductive connector sleeves 140, 150, 160, and 170 are provided and press-fittingly disposed respectively in through holes 340, 350, 360, and 370. Connector sleeve 140 is comprised of an outer surface 141, a distal end 142 including a distal bore 143, a central region 145, and a proximal end 146 including a proximal bore 147. Connector sleeves 150, 160, and 170 are similarly structured. The through holes 340, 350, 360 and 370 in feedthrough adapter holder/interconnector 310 are provided with diameters sized to enable a mild press fit of the connector sleeves disposed therein. The connector sleeves 140, 150, 160 and 170 are first press fitted into feedthrough adapter holder 310 such that each is engaged with the holder at its central region, e.g., connector sleeve 140 is engaged with through hole 340 at central region 145. Feedthrough adapter holder/interconnector 310 may further comprise grooves at opposed side walls 318 thereof. These grooves can be provided for additional engagement surface for a crimping assist tool 390 (see FIG. 7A) to contact when (a) the connector sleeves 140, 150, 160 and 170 are press fitted into the feedthrough adapter holder/interconnector 310, (b) vertically moving a portion of the adapter holder/interconnector 310 with respect to the connector sleeves and/or (c) crimping the connector sleeves to the feedthrough wires by horizontally moving a portion of the adapter holder/interconnector 310.

Figures 7A, 7B:
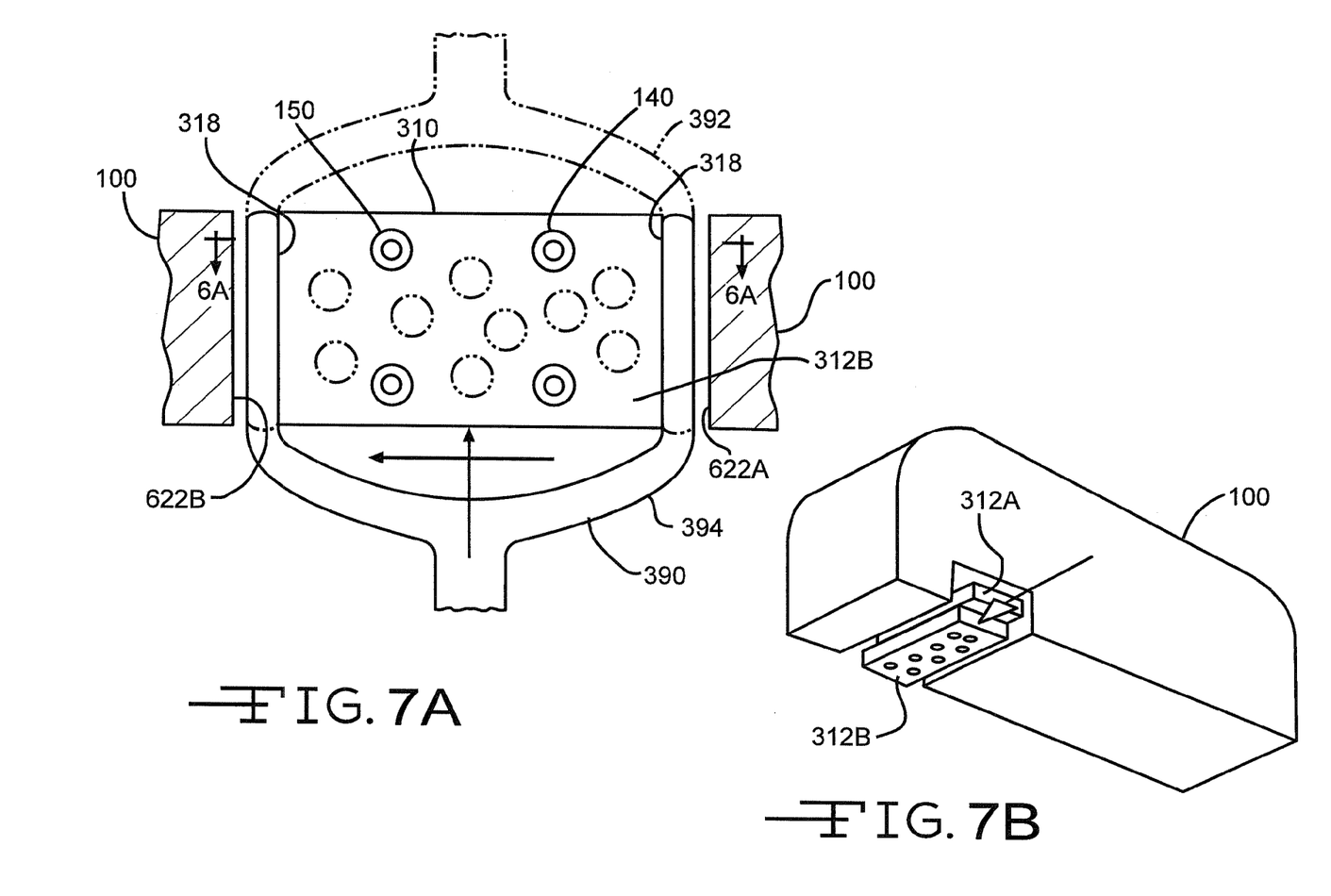
FIGS. 7A and 7B are schematic illustrations of one method for crimping a dense, non-linear, scattered arrangement of feedthrough wires of an implantable medical device to the connector sleeves of the conductor subassemblies of the header assembly.

The feedthrough adapter holder/interconnector 310 serves to precisely locate the connector sleeves 140, 150, 160 and 170 fitted therein during subsequent header assembly fabrication steps, and is particularly useful for header assemblies comprised of a high number of conductive subassemblies closely spaced in a dense, non-linear, scattered array as illustrated in FIG. 7A. Unlike prior methods, a laser is unable to connect those connector sleeves to respective feedthrough wires because the beam is unable to reach those locations at the interior of such a dense array. For similar reasons, a conventional crimping device is also unable to crimp the connector to the feedthrough wires in such a dense format.

In one exemplary embodiment, the connector sleeves are made of titanium, with a cylindrical shape, a length of about 0.13 inches, a diameter of about 0.03 inches, a distal bore of about 0.017 inches in diameter and a proximal bore of about 0.017 inches in diameter.

Figure 5:
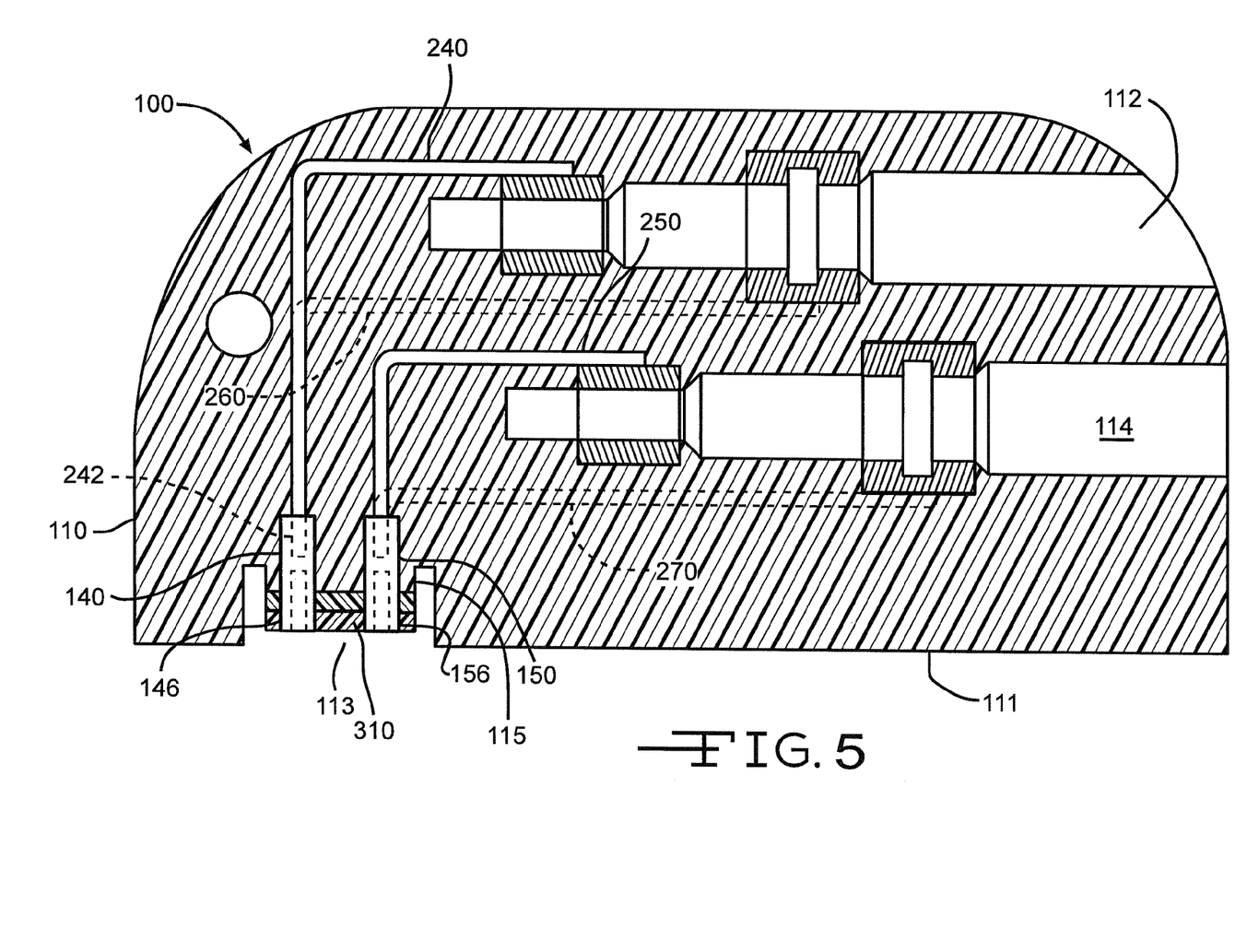
FIG. 5 is a cross-sectional view of conductor subassemblies of the header assembly placed in a mold, prior to molding the header body of the header assembly.

As shown in FIGS. 3 to 5, the proximal ends 146, 156, 166 and 176 of the respective connector sleeves 140, 150, 160 and 170 are positioned within the feedthrough adapter holder/interconnector 310. Intermediate conductor wires to be joined to the connector sleeves are then provided. This is best understood with reference to FIGS. 1, 4 and 5, which depict the intermediate conductor wires after the overall fabrication of the conductive subassemblies is completed. Conductor wires 240, 250, 260, and 270 are joined to the connector sleeves 140, 150, 160, and 170, respectively. Each of the conductor wires is comprised of a distal end, and a proximal end. The proximal ends of the conductor wires are disposed in the distal bores of the respective connector sleeves. For example, proximal end 242 of conductor wire 240 is disposed in distal bore 143 of connector sleeve 140.

The conductor wires are then joined to their respective connector sleeves. The joining is performed by laser welding the conductor wire proximal ends to the distal ends of the connectors. Alternatively, the joining may be accomplished by a press fit of the conductor wire proximal ends in the distal bores. In another alternative embodiment, the joining may be accomplished by crimping and/or resistance welding the conductor wires to the connector sleeves.

The partial subassemblies comprising of conductor wires 240, 250, 260 and 270 and connector sleeves 140, 150, 160 and 170 disposed within feedthrough adapter holder/interconnector 310 are then placed in a fixture (not shown) so that the distal ends of the conductor wires can be joined to terminals 245, 255, 265, and 275. The conductor wires 240, 250, 260 and 270 are preferably provided pre-formed into their respective desired shapes to be supported within the polymeric header body 110 (see FIG. 1) prior to the step of positioning the conductor wires in the fixture. Alternatively, the conductor wires 240, 250, 260 and 270 may be formed into the desired shapes when the feedthrough adapter holder/interconnector 310 has been secured in the fixture.

With the conductor wires formed and secured in the fixture in their respective desired shapes to be supported within the polymeric header body 110, terminals to be joined to the distal ends of conductor wires 240, 250, 260 and 270 are then provided. Suitable terminals, or terminal blocks, are as described in paragraphs 0029 to 0033 of the aforementioned U.S. Pat. No. 7,167,749 to Biggs et al. Terminals 245, 255, 265, and 275 are joined to the respective distal ends 244, 254, 264, and 274 of conductor wires 240, 250, 260, and 270 by resistance welding, laser welding, or another suitable joining process. The exemplary completed conductor subassembly 241 of FIG. 4 comprises the connector sleeve 140, conductor wire 240, and terminal 245. In the preferred embodiment, connector sleeve 140, wire 240, terminal 245, and the corresponding components of the other conductor subassemblies are made of titanium. Alternatively, these components may be made of a nickel-titanium alloy (MP35N®), stainless steel, platinum, iridium, niobium, palladium or another high purity biocompatible metal.

Referring again to FIG. 4, the cluster of conductor subassemblies aligned in a desired arrangement by the feedthrough adapter holder/interconnector 310 is placed in a mold 320. The mold comprises a mold body 322 and a mold cavity 324, and is formed in the desired shape of the molded header body 110. Of particular note is that the mold body 322 has spaced apart upstanding webs 322A and 322B that contact opposite side walls 318 of the holder/interconnector 310. These webs 322A, 322B occupy space immediately adjacent to the side walls 318 of the holder/interconnector 310 for later accessing the holder/interconnector 310 for at least crimping the connectors 140, 150 to the feedthrough wires.

A conductor lead mold insert 326 is preferably provided which includes two connector lead plugs 327 and 328 joined to a base plate 329. The use of connector mold insert 326 forms openings 112 and 114 (see FIG. 5) in the molded header body 110 in the shape of lead plugs 327 and 328, which are dimensioned substantially the same as connector lead 24 of FIG. 1. In this manner, the connector lead openings 112 and 114 are formed as part of the molding process, and do not need to be separately bored in a subsequent step.

The polymeric header body is then molded by injecting a polymeric melt from nozzle or die 321 through port 323 into the mold cavity 324. The polymeric melt fills mold cavity 324, thereby forming a monolithic structure surrounding the conductor subassemblies and the mold inserts therein. Suitable moldable polymeric materials for header body 110 include urethanes, such as e.g., TECOTHANE®, an aromatic polyether-based thermoplastic polyurethane sold by the Thermedics Polymeric Products Company of Wilmington, Mass.

Once the polymeric header body is formed, the mold is removed through conventional processes from the header body 110.

FIG. 5 is a cross-sectional view of one embodiment of a finished header assembly 100 including the conductor subassemblies and the monolithic molded header body 110 after the header assembly has been removed from the mold 320 and the conductor lead mold insert 326 has been removed from header body 110. Unlike the prior art processes which use a unitary feedthrough adaptor holder exclusively for the molding process and remove the feedthrough adaptor holder from the header body prior to assembling the header body with the medical device, the feedthrough adapter holder/interconnector 310 remains at the proximal ends of the connector sleeves.

The resulting gap 113 in the header body 110 has an extended boss 115 as illustrated at FIG. 5, with the holder/interconnector 310 protruding downwardly toward the bottom surface 111 of the insulative material. Since it is important to have the proximal bores of the connector sleeves mate properly with the feedthrough wires of the implantable device, it is preferable that the connectors are precisely located and rigidly supported by the body of the header assembly and the holder/interconnector 310. In that respect, the extended boss 115 and the holder/interconnector 310 provides improved support at the distal end and central region of each of the connector sleeves while the proximal connector ends including the proximal bores are disposed within the gap 113. For example, proximal end 146 of connector sleeve 140 is disposed in gap 113.

It is to be understood that the header assemblies, subcomponents, and associated tools described and shown herein are exemplary. The molded header can have a myriad of different shapes only limited by the design specifications of the associated medical device and its intended use. Additionally, it is not required that the header assemblies shown in the accompanying drawings have any particular number of conductor subassemblies, and are thus not limited to connection to implantable devices comprising any particular number of feedthrough wires. While the header assemblies of the present invention are particularly useful when dense arrays of conductor subassemblies are required therein for connection to numerous feedthrough wires, the instant header assemblies may be comprised of only a single conductor subassembly.

In one exemplary embodiment (not shown), the header assembly is comprised of six conductor subassemblies with the proximal ends of the six connector sleeves exposed in gap 113. The six conductors are preferably disposed in a hexagonal arrangement. In another exemplary embodiment, the header assembly is comprised of eight conductor subassemblies with the proximal ends of the eight connector sleeves exposed in gap 113. The eight conductors are preferably disposed in an arrangement of two groups of four. In another embodiment, the conductors are disclosed in a dense, non-linear, scattered format as illustrated in FIGS. 7A and 7B.

Figure 6A:
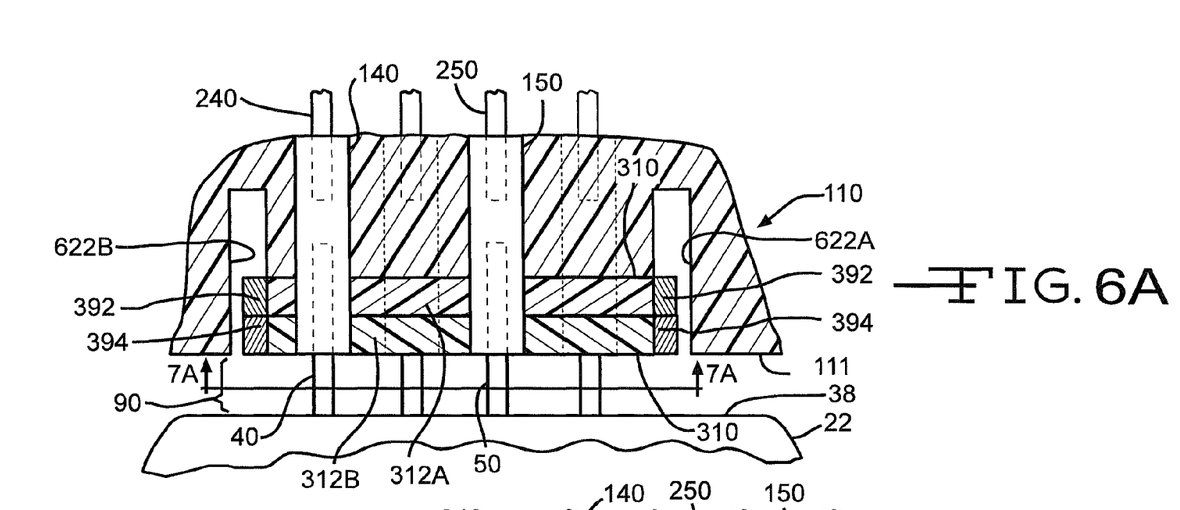
Figure 6B:
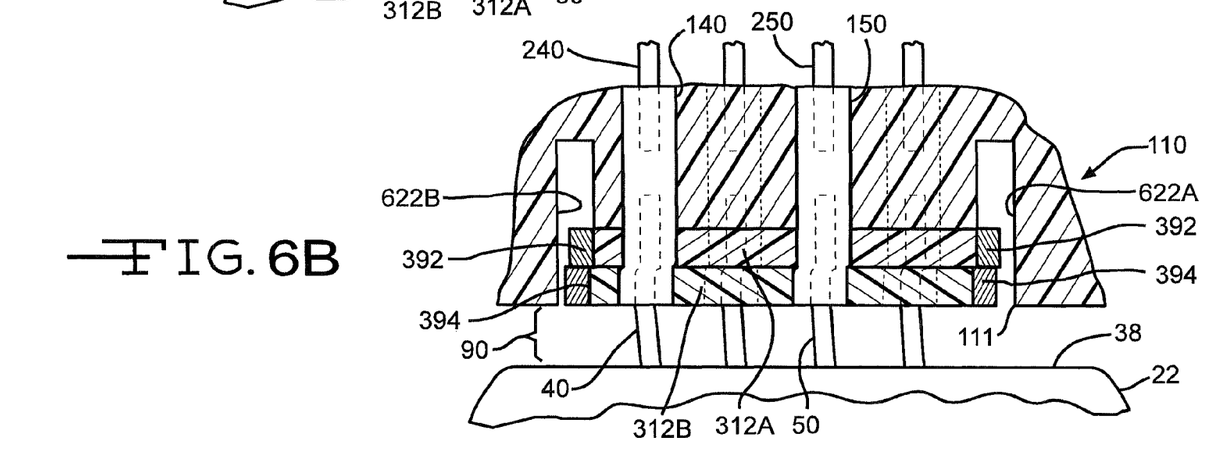

As shown in FIGS. 6A and 6B, the header assembly 100 of FIG. 5 is connectable to an implantable device. In general, a method for connecting header assembly 100 to an implantable device includes the steps of connecting the conductor subassemblies therein to the feedthrough wires of the device, and sealing the header assembly to the housing of the device. FIGS. 6A, 6B, 7A and 7B illustrate a schematic illustration of one method for crimping the feedthrough wires to the connector sleeves of the conductor subassemblies. The method begins by positioning header assembly 100 proximate to the implantable device 22 in a fixture (not shown). The feedthrough wires of the device 22 are now aligned along a longitudinal axis disposed in the proximal bores of the connector sleeves of the conductor subassemblies. For example, feedthrough wire 40 is disposed in connector sleeve 140, and feedthrough wire 50 is disposed in connector sleeve 150 as shown in FIG. 6A. The bottom surface 111 of the insulative body 110 is proximate to the upper surface 38 of the wall of the housing 110, with an interstice 90 formed there between. Interstice 90 is depicted in FIGS. 6A and 6B for illustrative purposes and may be considerably narrower than shown.

With the header assembly 100 positioned as shown with respect to the implantable device 22, the feedthrough wires of the device are joined to the connector sleeves of the header assembly 100. This is done by positioning a crimping assist tool 390 comprising two pincers 392, 394 into the space 622A, 622B previously occupied by the webs 322A and 322B of the mold body 322. Pincer 392 contacts the holder/interconnector's upper plate's 312A side walls and pincer 394 contacts the holder/interconnector's lower plate's 312B side walls. For illustration purposes in FIG. 7A, pincer 392 and pincer 394 are on opposite sides of the holder/interconnector 312. The pincers 392, 394 can be on opposite sides or the same side of the holder/interconnector.

Figure 8:
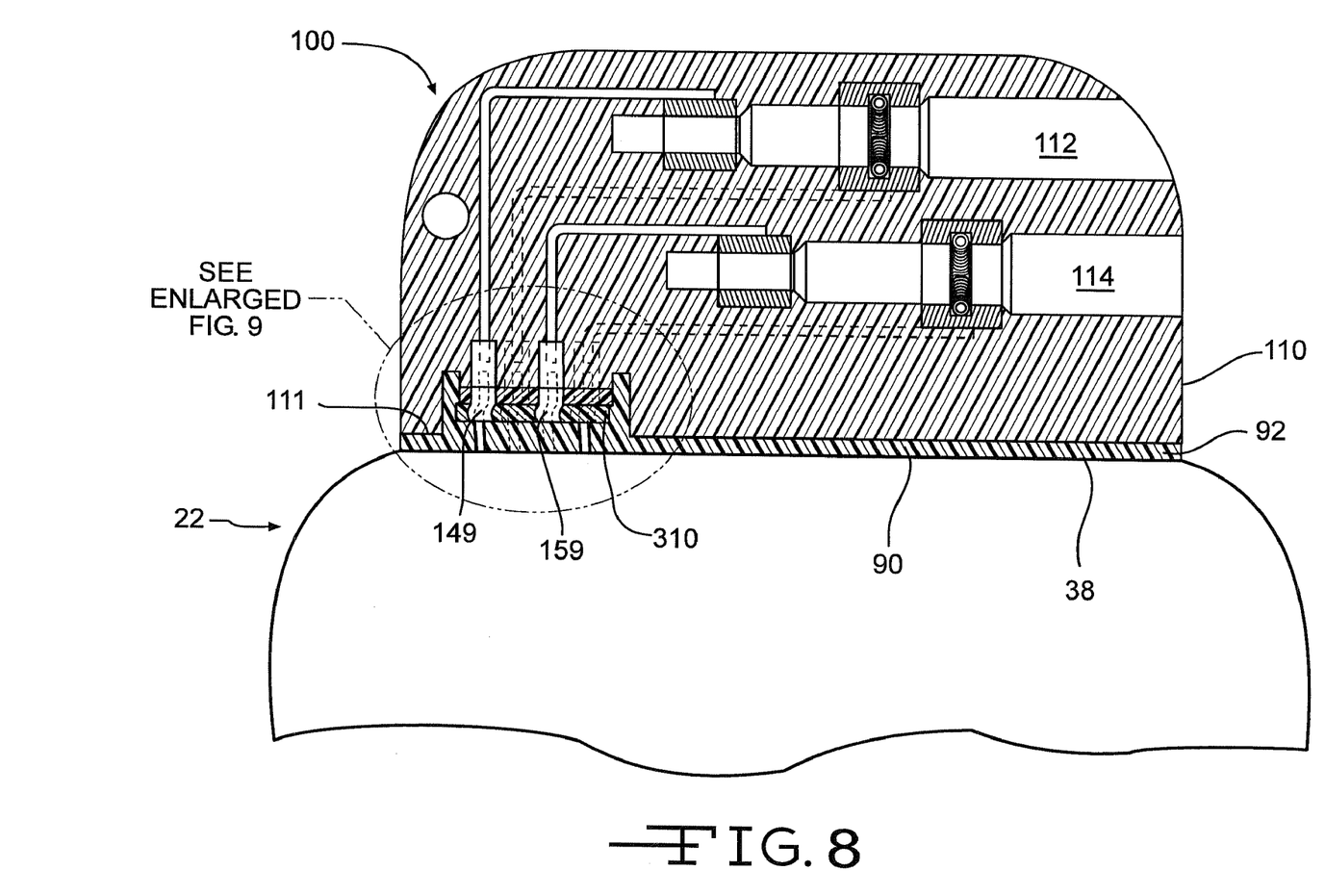
Figure 9:
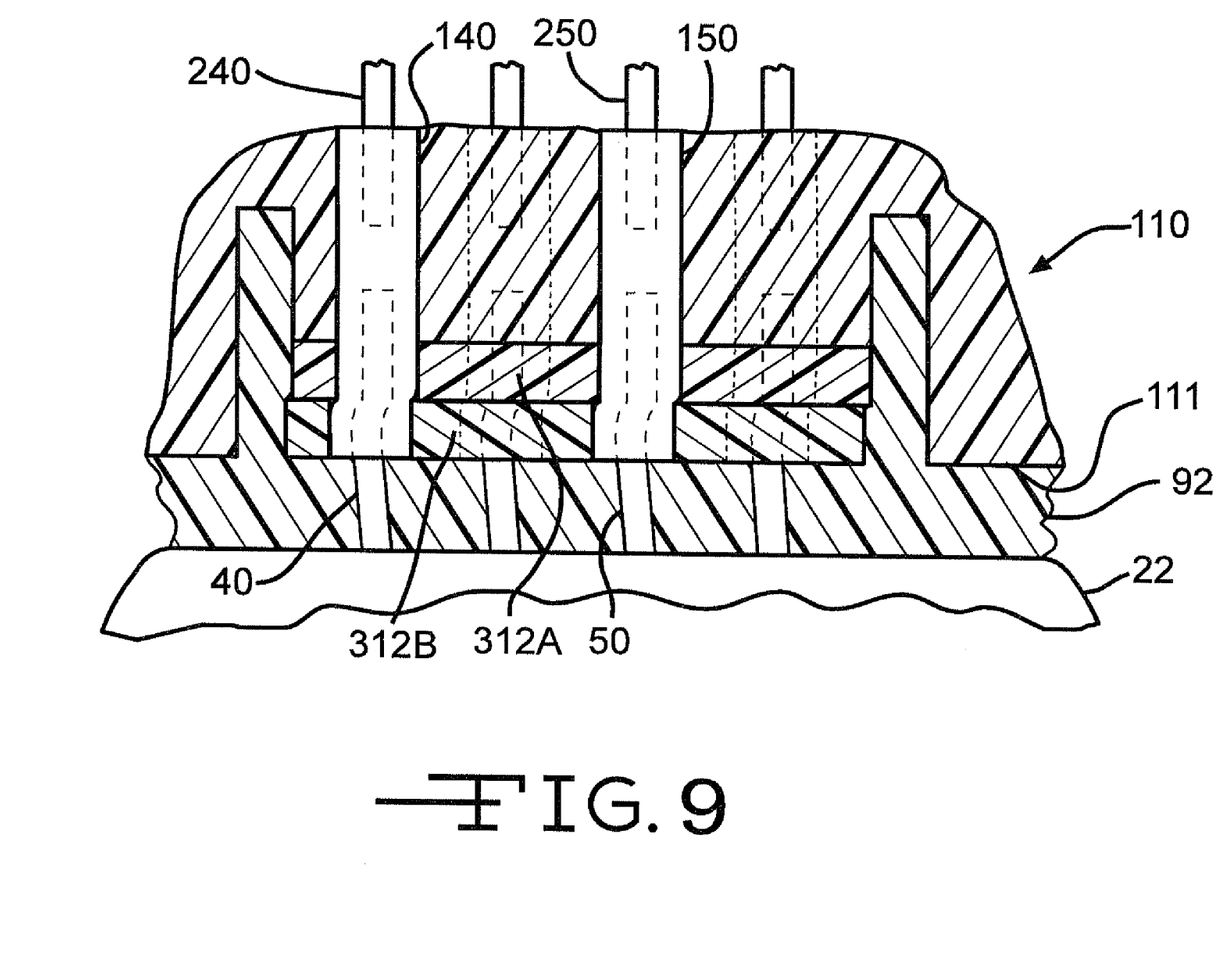
FIG. 9 is an enlarged embodiment of FIG. 8.

Next, as illustrated in FIG. 7B the upper pincer 392 is moved in a first direction while the lower pincer 394 is either moved in an opposite direction or not moved at all; and vice versa. This results in the connector wall material surrounding the feedthrough wire being securely crimped to the feedthrough wire, as illustrated in FIGS. 6B, 8 and 9. Referring to FIG. 8, crimping area 149 and 159 are made between the respective connector sleeves and feedthrough wires.

With the connector sleeves joined to their respective feedthrough wires, the header assembly 100 is then secured to the implantable device 22. In one embodiment, a curable liquid sealant is discharged into the interstice 90 between the header assembly 100 and the implantable device 22. Referring to FIGS. 8 and 9, liquid sealant 92 is inserted into and fills interstice 90 and gap 113 between assembly 100 and device 22 (which also includes the holder/interconnector 310). Within a predetermined time frame and under conventional methods which include and are not limited to light, ultrasonic, and/or thermal energy, the liquid sealant cures. The cured liquid sealant 92 seals the welded connector sleeves and feedthrough wires embedded therein, and joins the assembly 100 to the device 22. In one embodiment, the cured liquid sealant 92 may consist essentially of an organopolysiloxane, also known generally as "silicone rubber." One suitable organopolysiloxane is Med-4211, sold by the Nusil Company of Carpiytia, Calif.

This invention is most practical when the feedthrough wires are in a dense, non-linear, scattered format or arrangement as illustrated and not limited to FIG. 7A. That is because this method allows the manufacturer to position feedthrough connectors and conductor wires in any position, not just positions that allow them to be laser welded or conventionally crimped. Laser welding and conventional crimping devices are applicable when the feedthrough wires are in a linear format that makes them readily accessible in a "line of sight" manner, and not when they are densely packed or tightly scattered in a confined space. However, the present invention is not intended to be limited for use with only densely packed arrangements of feedthrough wires connected to connector sleeves. Instead, it is useful with any number of such assemblies provided in any desired arrangement or spacing configuration with respect to each other.

It is, therefore, apparent that there has been provided, in accordance with the present invention, a header assembly for connecting an implantable medical device to at least one conductor lead terminating within a patient intended to be assisted by the medical device, and methods for making the header assembly, and for connecting the header assembly to the implantable medical device. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. An implantable medical device, which comprises:
   a) a housing containing control circuitry, at least one electrical energy storage device, and at least one feedthrough wire extending from the control circuitry and through a wall of the housing to a distal portion of the wire;
   b) an insulative body mounted on the housing of the medical device;
   c) at least one terminal supported by the insulative body and that is directly connectable to at least one medical lead;
   d) at least one conductor wire supported by the insulative body and comprising a distal end that is electrically connected to the terminal spaced from a proximal conductor wire end; and
   e) at least one connector sleeve supported by the insulative body and comprising a sidewall extending along a longitudinal axis from a distal sleeve portion including a distal sleeve bore to a proximal sleeve portion including a proximal sleeve bore,
      i) wherein the proximal conductor wire end is disposed within the distal sleeve bore and electrically connected thereto, and
      ii) wherein the distal portion of the at least one feedthrough wire resides in the proximal sleeve bore with the sleeve sidewall crimped into an electrical connection therewith as an effect of a lateral force generally perpendicular to the longitudinal axis having been imparted to the connector sleeve such that a lower region of the proximal sleeve portion is laterally offset from an upper region of the proximal sleeve portion to thereby physically connect the connector sleeve the feedthrough wire at the lateral offset.

2. The implantable medical device of claim 1 comprised of a plurality of feedthrough wires extending from the control circuitry and through a wall of the housing, and wherein the insulative body supports a corresponding plurality of conductor wires electrically connected between respective terminals and connector sleeves crimped to the feedthrough wires.

3. The implantable medical device of claim 2 wherein the insulative body is comprised of an extended boss supporting the distal end and a central region of the at least one connector sleeve.

4. The implantable medical device of claim 1 wherein the insulative body is of a molded polymeric material.

5. The implantable medical device of claim 1 wherein the terminal, the conductor wire, and the connector sleeve are each selected from the group consisting of titanium, nickel-titanium alloy, stainless steel, platinum, iridium, niobium, palladium, and mixtures thereof.

6. The implantable medical device of claim 1 wherein the connector sleeve is of a cylindrical shape.

7. The implantable medical device of claim 1 being selected from the group consisting of a hearing assist device, a neurostimulator, a cardiac pacemaker, a drug pump, a cardiac defibrillator, and an obesity control device.

8. An implantable medical device, which comprises:
   a) a housing containing control circuitry, at least one electrical energy storage device, and at least one feedthrough wire extending from the control circuitry and through a wall of the housing to a distal portion of the wire;
   b) an insulative body mounted on the housing of the medical device;
   c) at least one terminal supported by the insulative body and that is directly connectable to at least one medical lead;
   d) at least one conductor wire supported by the insulative body and comprising a distal end that is electrically connected to the terminal spaced from a proximal conductor wire end; and
   e) at least one connector sleeve supported by the insulative body and comprising a sidewall extending along a longitudinal axis from a distal sleeve portion including a distal sleeve bore to a proximal sleeve portion including a proximal sleeve bore; and
   f) upper and lower plates supported by the insulative body and comprising respective upper and lower plates bores housing the proximal sleeve portion,
      i) wherein the distal conductor wire end is disposed within the distal sleeve bore and electrically connected thereto, and
      ii) wherein a proximal portion of the at least one feedthrough wire resides in the proximal sleeve bore with the outer sleeve sidewall crimped into an electrical connection with the feedthrough wire as an effect of the upper plate bore being out of direct alignment with the lower plate bore along the longitudinal axis of the sleeve.

9. The implantable medical device of claim 8 wherein the crimp is characterized as having been formed as a result of a first lateral force imparted generally perpendicular to the longitudinal axis against one of the upper and lower plates in respect to the other plate.

10. The implantable medical device of claim 9 wherein the crimp is characterized as having been formed as a result of a second lateral force generally opposite that of the first lateral force having been imparted to the other plate.

11. The implantable medical device of claim 9 wherein the crimp is characterized as having been formed as a result of no lateral force having been imparted to the other plate.

12. An implantable medical device, which comprises:
   a) a housing containing control circuitry, at least one electrical energy storage device, and at least one feedthrough wire extending from the control circuitry and through a wall of the housing to a distal portion of the wire;
   b) an insulative body mounted on the housing of the medical device;
   c) at least one terminal supported by the insulative body and that is directly connectable to at least one medical lead;
   d) at least one conductor wire supported by the insulative body and comprising a distal end that is electrically connected to the terminal spaced from a proximal conductor wire end; and
   e) at least one connector sleeve supported by the insulative body and comprising a sidewall extending along a longitudinal axis from a distal sleeve portion to a proximal sleeve portion including a proximal sleeve bore,
      i) wherein the proximal conductor wire end is electrically connected to the distal sleeve portion, and
      ii) wherein the distal portion of the at least one feedthrough wire resides in the proximal sleeve bore with the sleeve sidewall crimped into an electrical connection therewith as an effect of a lateral force generally perpendicular to the longitudinal axis having been imparted to the connector sleeve such that a lower region of the proximal sleeve portion is laterally offset from an upper region of the proximal sleeve portion to thereby physically connect the connector sleeve to the feedthrough wire at the lateral offset.

* * * * *